United States Patent
Viala

(10) Patent No.: US 11,097,341 B2
(45) Date of Patent: Aug. 24, 2021

(54) METHOD FOR MANUFACTURING METAL/POLYMER HYBRID NANOPARTICLES WITH NARROW SIZE DISTRIBUTION BY MINIEMULSION POLYMERISATION

(71) Applicant: COMMISSARIAT A L'ENERGIE ATOMIQUE ET AUX ENERGIES ALTERNATIVES, Paris (FR)

(72) Inventor: Bernard Viala, Grenoble (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 0 days.

(21) Appl. No.: 16/787,087

(22) Filed: Feb. 11, 2020

(65) Prior Publication Data
US 2020/0261972 A1  Aug. 20, 2020

(30) Foreign Application Priority Data
Feb. 18, 2019  (FR) .................. 19 01599

(51) Int. Cl.
*B22F 1/02* (2006.01)
*B22F 9/00* (2006.01)
(Continued)

(52) U.S. Cl.
CPC .......... *B22F 1/02* (2013.01); *B22F 9/00* (2013.01); *B22F 2302/40* (2013.01);
(Continued)

(58) Field of Classification Search
CPC .................. B22F 1/02; B22F 9/00
(Continued)

(56) References Cited

U.S. PATENT DOCUMENTS

| 2010/0123996 | A1 | 5/2010 | Imanaka |
| 2015/0197660 | A1* | 7/2015 | Ronne .......... C08J 3/09 524/432 |
| 2020/0265997 | A1* | 8/2020 | Viala .......... H01G 4/08 |

FOREIGN PATENT DOCUMENTS

EP       3 252 782 A1   12/2017

OTHER PUBLICATIONS

U.S. Appl. No. 15/988,097, filed May 24, 2018, 2018/0342343 A1, Viala, et al.
(Continued)

*Primary Examiner* — Weiping Zhu
(74) *Attorney, Agent, or Firm* — Oblon, McClelland, Maier & Neustadt, L.L.P.

(57) ABSTRACT

Method for manufacturing nanoparticles comprising a metallic core coated with a layer of polymer material comprising the following steps:
a) preparing a water-in-oil emulsion comprising droplets of an aqueous phase, dispersed in an organic phase,
b) adding nanoparticles comprising a metallic core coated with a shell of carbonaceous material, whereby nanoparticles trapped in the droplets are obtained,
c) adding precursor monomers of the polymer material, and
d) adding a polymerisation initiator,
adding the precursor monomers and the polymerisation initiator resulting in polymerisation of the monomers, whereby nanoparticles coated with a layer of polymer material dispersed in the organic phase are obtained.

11 Claims, 6 Drawing Sheets

(51) Int. Cl.
  *B82Y 5/00* (2011.01)
  *B82Y 30/00* (2011.01)
  *B82Y 40/00* (2011.01)

(52) U.S. Cl.
  CPC ............ *B22F 2302/45* (2013.01); *B82Y 5/00* (2013.01); *B82Y 30/00* (2013.01); *B82Y 40/00* (2013.01)

(58) Field of Classification Search
  USPC .......................................................... 75/330
  See application file for complete search history.

(56) References Cited

OTHER PUBLICATIONS

French Preliminary Search Report dated Dec. 4, 2019 in French Application 19 01599, filed on Feb. 18, 2019 (with English Translation of Categories of Cited Documents), 2 pages.
French Preliminary Search Report dated Dec. 5, 2019 in French Application 19 01600, filed on Feb. 18, 2019 (with English Translation of Categories of Cited Documents), 2 pages.
H. Takacs et al. "Non-conductive ferromagnetic carbon-coated (Co, Ni) metal/polystyrene nanocomposites films". Journal of Applied Physics 119, 2016, 10 pages.
H. Takacs et al. "Non-conductive ferromagnets based on core double-shell nanoparticles for radio-electric applications", Springer Plus, 2016, 9 pages.
Y. Shen et al. "High Dielectric Performance of Polymer Composite Films Induced by a Percolating Interparticle Barrier Layer", Advanced Materials, vol. 19, 2007, pp. 1418-1422.
V. Herman et al. "Core double-shell cobalt/graphene/polystyrene magnetic nanocomposites synthesized by in situ sonochemical polymerization", RSC Advances, vol. 5, 2015, pp. 51371-51381.
Y.Shen et al. "Interfacial Effect on Dielectric Properties of Polymer Nanocomposites Filled With Core/Shell-Structured Particles", Advanced Functional Materials, vol. 17, 2007, pp. 2405-2410.
J. Quinsaat et al. "Chapter 5: Surface Hydrophobization of Silver Nanoparticles (AgNPs) through Surface-initiated Atom Transfer Radical Polymerization (SI-ATRP)", 2015, 24 pages.
B. Chu et al. "A Dielectric Polymer with High Electric Energy Density and Fast Discharge Speed", Science vol. 313, 2006, 5 pages.
Y. Wu et al. "Graphene/Boron Nitride—Polyurethane Microlaminates for Exceptional Dielectric Properties and High Energy Densities", Applied Materials & Interfaces, vol. 10, 2018, 12 pages.

* cited by examiner

METHOD FOR MANUFACTURING METAL/POLYMER HYBRID NANOPARTICLES WITH NARROW SIZE DISTRIBUTION BY MINIEMULSION POLYMERISATION

TECHNICAL FIELD

The present invention relates to the field of metal-polymer nanocomposite materials of defined dimensions, and particularly to the manufacture of core/shell structure nanoparticles.

More specifically, it relates to a method for manufacturing nanoparticles with a narrow size distribution comprising a metallic core coated with a layer of polymer material.

The invention also relates to a nanoparticle powder obtained with such a method and to a use of such a powder.

The present invention finds applications in the field of electromagnetism, from optics to energy conversion, or indeed biology.

STATE OF THE RELATED ART

Metal-polymer hybrid nanoparticles are used in numerous fields: biomedical, coatings (antimicrobial and antifungal for example), paint, optics, electronics, magnetism, and catalytic systems.

Metal-polymer hybrid nanoparticles are nanoparticles comprising a metallic core coated with a polymer.

Conventionally, to manufacture such materials, suspended metallic nanoparticles are mixed with a solution containing a dissolved polymer.

For example, in the article by Shen et al. ("High dielectric performance of polymer composite films induced by a percolating interparticle barrier layer", Advanced Materials 2007, 19(10), 1418-1422), a thin layer of polymer (PVP) is grafted around silver nanoparticles hydrothermally. For this, glucose, polyvinylpyrrolidone (PVP) and $AgNO_3$ (0.1 M) are mixed in an aqueous solution. The solution is then sealed in an autoclave kept at 180° C. for 4 h, after centrifugation and washing, the coated nanoparticles are retrieved.

When the nanoparticle surface is made of carbon, polymer grafting is facilitated, $\pi$-$\pi$ bonds are readily formed by delocalised electron transfer, between the polymer and the nanoparticle surface. However, these bonds are weaker than covalent bonds and the mechanical stability over time is lower.

In order to form covalent bonds between a polymer and nanoparticles, it is possible to carry out in-situ polymerisation using monomers. In-situ polymerisation involves free radicals which naturally promote covalent bond formation. Such polymerisation is, for example, described in the article by Herman et al. ("Core double-shell cobalt/graphene/polystyrene magnetic nanocomposites synthesized by in situ sonochemical polymerization", RSC Advances (2015), 5(63), 51371-51381). Cobalt nanoparticles coated with graphene in multilayers are mixed with styrene and a polymerisation initiator. The polymerisation is carried out in the presence of ultrasound (i.e. by sonochemistry) with a power of 100 W.

However, in order to carry out the polymerisation process, it is necessary to supply a large quantity of cavitation energy in a homogeneous mixture of nanoparticles and monomers. This method may result in damage to the nanoparticles, in particular in degradation of the graphene shell and/or oxidation of the graphene and/or of the metallic core of the nanoparticles which is no longer fully protected by the graphene.

Furthermore, the final size of the metal/polymer hybrid nanoparticles is dependent on the initial size of the starting nanoparticles. However, frequently the powders have a wide size dispersion which can range from less than 5 nm to more than 300 nm. However, it is important to be able to provide monodispersed metal/polymer hybrid nanoparticles since the properties of the nanoparticles are frequently associated with the size thereof. For example, in the field of capacitors, nanodielectric composite materials are subject to uncontrolled breakdown fields when the nanoparticle size is too dispersed. In the field of inductors, excessively small nanoparticles are ineffective (non-magnetic at ambient conditions) and very large nanoparticles cause high-frequency ohmic losses (eddy currents).

DESCRIPTION OF THE INVENTION

An aim of the present invention is that of providing a method for manufacturing nanoparticles comprising a metallic core coated with a layer of polymer material of defined thickness, having a narrow size distribution, the layer of polymer material being intended to have a good mechanical resistance over time.

For this, the present invention relates to a method for manufacturing nanoparticles comprising a metallic core coated with a layer of polymer material, the method comprising the following steps:

a) preparing a water-in-oil emulsion comprising droplets of an aqueous phase, dispersed in an organic phase, b) adding nanoparticles comprising a metallic core coated with a shell of carbonaceous material, whereby nanoparticles trapped in the droplets are obtained, c) adding precursor monomers of the polymer material, and d) adding a polymerisation initiator.

contacting the precursor monomers of the polymer material and the polymerisation initiator results in polymerisation of the monomers, whereby nanoparticles coated with a layer of polymer material, dispersed in the organic phase, are obtained.

The invention differs fundamentally from the prior art by the in-situ formation of a layer of polymer of controlled thickness around a nanoparticle of defined size in an emulsion.

Emulsion denotes a heterogeneous mixture of two non-miscible liquids, such as oil and water. One of the two phases (so-called dispersed phase, herein the aqueous phase) is dispersed in droplet form in the other (so-called dispersing phase). The size of the droplets may range from some tens of nanometres to several microns.

The droplets act both as a filter and as a polymerisation reactant.

Only nanoparticles wherein the diameter is less than the diameter of the droplets will be trapped in the droplets and coated with a layer of polymer during the method.

Nanoparticles wherein the diameter is greater than or equal to that of the droplets will form a raw sediment (with no polymer) which will be readily subsequently removed. Moreover, it has been observed that the smallest nanoparticles (for example of a diameter of less than 10 nm) are imperfectly coated with the carbonaceous layer and are oxidised rapidly, giving them a more hydrophobic nature than nanoparticles fully coated with a carbonaceous layer. These particles do not enter the droplets containing the aqueous phase and remain suspended in the dispersing phase and can be readily subsequently removed.

The droplets form micelles which are microreactors wherein the polymerisation reaction takes place. During the polymerisation reaction, the monomers will be progressively consumed until the micelle is saturated. This is referred to as micellar growth. The size of the final particle formed is similar to that of the micelle. In the end, a product referred to as latex is obtained, comprising monodispersed polymer beads (micelles without metallic nanoparticle) and metal-polymer hybrid nanoparticles (micelles with metallic nanoparticles).

The metallic nanoparticles are coated with a layer of carbonaceous material (metal/C nanoparticles where C represents the layer of carbonaceous material), to effectively protect the nanoparticles against oxidation and give them hydrophilic properties. The nanoparticles can thus enter the droplets containing the aqueous phase. The carbonaceous layer forms, advantageously, a continuous layer around each nanoparticle. Without this carbonaceous shell, the metallic nanoparticles would oxidise spontaneously in contact with water and/or would form metal hydroxides, which would render them hydrophobic and contribute to them being expelled from the micelles to join the dispersing phase (oil).

Advantageously, the carbonaceous material is organized 2D carbon. Preferably, the carbonaceous material is graphene. The carbonaceous layer is formed from a repetition of some layers to some tens of layers of graphene to retain a 2D organised carbon structure. For example, it comprises some layers of graphene (from 2 to 5 for example). Advantageously, a carbonaceous layer comprising at least two layers of graphene will be chosen to give the nanoparticle sufficient hydrophilic properties and to be able to form Van der Waals bonds. Advantageously, a number of layers less than 100 will be chosen, to prevent the appearance of defects in the layers and have a disorganised 2D carbon arrangement on the surface, for example hydrogenated, or of graphitic type which are hydrophobic.

Advantageously, the core of the nanoparticles is made of cobalt, iron, nickel, copper, silver, gold, or of one of the alloys thereof, or of one of the nitrides thereof. For example, alloys of cobalt and iron (CoFe), of cobalt, iron and nickel (CoFeNi), of nickel and iron (NiFe) or iron nitrides $Fe_4N$ or $Fe_{16}N_2$ will be chosen.

Advantageously, the polymer material is chosen among polystyrene, poly(methyl methacrylate), polyurethane, a polyacrylic, polypropylene, a polyimide, polyetherimide and a polymer having pyrene groups.

Advantageously, the thickness of the layer of polymer material ranges from 1 nm to 100 nm, preferably from 2 nm to 50 nm, and even more preferentially from 5 nm to 15 nm.

Advantageously, the diameter of the droplets ranges from 20 nm to 1 µm. The mean micelle size is readily adaptable to that of the nanoparticles sought. Advantageously, micelles will be chosen having a slightly larger size than that of the nanoparticles to be trapped to be able to introduce the latter selectively into the micelles without destabilising the emulsion.

Advantageously, the diameter of the droplets ranges from 30 nm to 100 nm.

Advantageously, electrically insulating nanoparticles are added to the emulsion. The particles are, advantageously, hydrophobic so as to be dispersed in the organic phase with the monomers. During polymerisation, some of these electrically insulating nanoparticles are carried by the monomers and find themselves trapped in and/or on the polymer layer coating the metallic nanoparticle.

Advantageously, the electrically insulating nanoparticles are made of metal oxide (for example $SiO_2$, $Al_2O_3$, $TiO_2$, $HfO_2$, $Ta_2O_5$, $BaTiO_3$ or $SrTiO_3$). Even more advantageously, the electrically insulating nanoparticles are made of a semiconductor material, preferably wide-bandgap, such as silicon carbide, diamond and/or hexagonal boron nitride. In the case of hexagonal boron nitride, they may also consist of nanotubes and/or nanoplates.

The polymerisation method in dispersed medium has numerous advantages with respect to conventional polymerisation in homogeneous medium. In particular, it makes it possible to:

graft a polymer covalently onto metallic nanoparticles without significant oxidation of the nanoparticles which retain the initial properties thereof (for example magnetic and/or electrical), control the thickness of the polymer (for example 5, 10 or 15 nm) more finely with respect to the so-called ex-situ grafting of a pre-existing polymer mixed with the nanoparticles, disperse the nanoparticles homogeneously in the emulsion, limit or eliminate the presence of aggregates, control the reaction temperature readily, lower the viscosity of the reaction medium (main problem with polymers), obtain a ready-to-use composite material (colloid or powder).

Furthermore, the method is simple to implement and requires little raw material.

The invention also relates to a nanoparticle powder obtained by the method described above, the nanoparticles comprising a metallic core coated successively with a layer of carbonaceous material and with a layer made of a polymer material, the nanoparticles having a low polydispersity (i.e. a narrow size distribution).

Low polydispersity denotes the absence of aggregates or very large nanoparticles (for example having a larger size, or larger dimension, up to 100 times, 30 times or 10 times larger than the mean nanoparticle size) and the absence of very small particles (having a size, for example, up to 6 times or 10 times smaller than the mean nanoparticle size). The ratio between the maximum nanoparticle diameter and the minimum nanoparticle diameter is less than or equal to 5, preferably less than or equal to 3.

Advantageously, the maximum/minimum nanoparticle diameter ratio is less than or equal to 2 and even more advantageously less than or equal to 1.5. Such a very narrow size distribution is enabled by the miniemulsion method described above.

Polymerisation in heterogeneous medium requires fewer radicals and less oxidant. Advantageously, the nanoparticles, for example, having a cobalt or iron core, obtained by this method, have magnetic properties, they have a magnetisation greater than or equal to 100 emu/g.

The invention also relates to a use of a nanoparticle powder as defined above, to embody an inductor, a filter, or a capacitor. For example, it consists of an inductor, a filter (low-pass, high-pass, passband, band-cut or common mode filter) or a capacitor made of thin layers on a substrate, preferably, made of silicon. Further substrates may be used such as glass, alumina, ferrite and polymer films such as for example polyimide (such as Kapton), polyethylene naphthalate (PEN), and polyethylene terephthalate (PET).

The invention also relates to an electronic device such as an inductor, a filter or a capacitor, for example an inductor, a filter or a capacitor made of thin layers on a substrate, preferably, made of silicon, comprising nanoparticles, as defined above, dispersed in a matrix. The use of such particles, for example, in a capacitor makes it possible to increase the permittivity significantly.

The matrix is, advantageously, a mineral or polymer matrix.

Advantageously, the matrix is made of a polymer material chosen among polystyrene, polyethylene terephthalate, cellulose acetate, polycarbonate, polypropylene, polyethylene, a polyamide, a polysiloxane, a polysulphone, an optionally aromatic polyester, a polyetheretherketone, a polyetherimide and an epoxide.

Advantageously, the polymer material comprises groups photosensitive to ultraviolet rays.

Advantageously, the matrix further includes electrically insulating nanoparticles.

Further features and advantages of the invention will emerge from the following supplementary description.

Obviously, this supplementary description is merely given by way of illustration of the subject matter of the invention and should in no way be interpreted as a restriction of this subject matter.

BRIEF DESCRIPTION OF THE DRAWINGS

The present invention will be understood more clearly on reading the description of embodiment examples given merely by way of indication and not restriction with reference to the appended drawings wherein.

Figure 1:
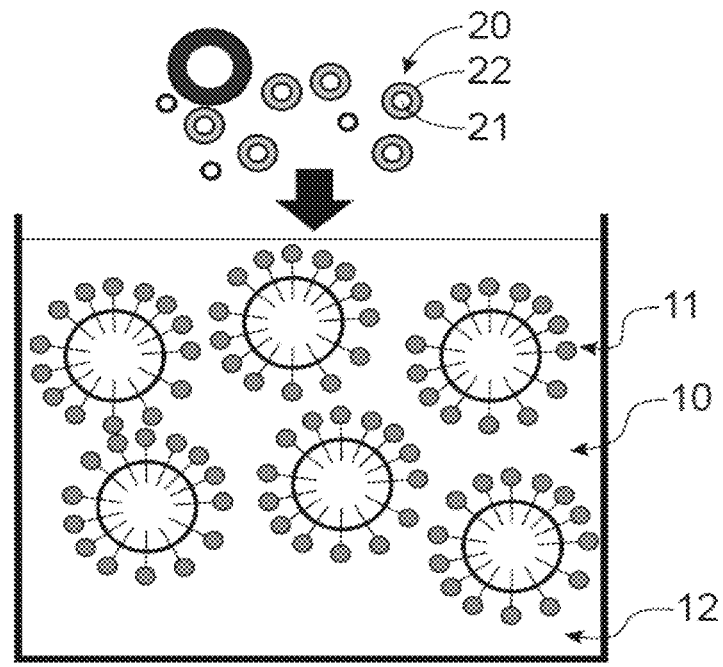
FIGS. 1, 2, 3, 4 and 5 represent different steps of a particular embodiment of the method according to the invention.

The different parts represented in the figures are not necessarily represented according to a uniform scale, to render the figures more legible.

The different possibilities (alternative embodiments and embodiments) should be understood as not being mutually exclusive and may be combined with one another.

DETAILED DESCRIPTION OF PARTICULAR EMBODIMENTS

Reference is made, firstly, to FIGS. 1 to 5 which represent the different steps of a method for coating nanoparticles 20 with a layer of polymer 23 of controlled thickness. The method comprises the following steps:

a) preparing a water-in-oil emulsion 10 comprising droplets 11 of an aqueous phase, dispersed in an organic phase 12 (FIG. 1), b) adding nanoparticles 20 comprising a metallic core 21 coated with a shell of carbonaceous material 22, whereby nanoparticles 20 trapped in the droplets 11 are obtained (FIG. 2), c) adding precursor monomers of the polymer material, and d) adding a polymerisation initiator.

Figure 3:
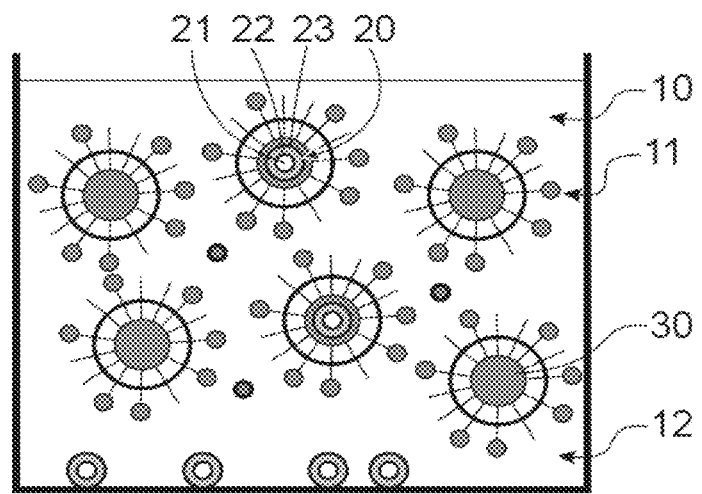
Figure 4:
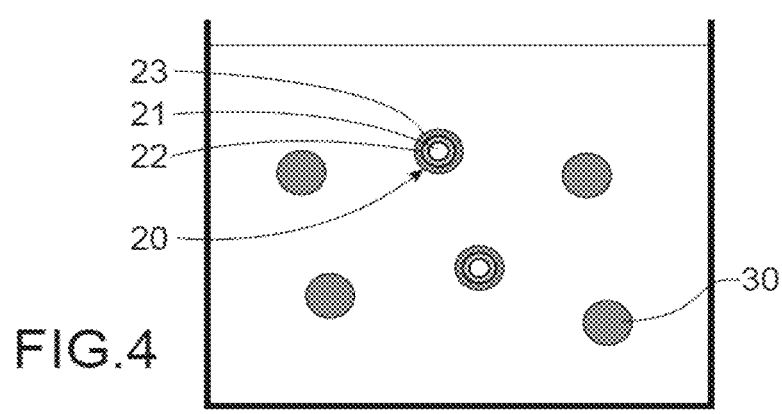
Figure 5:
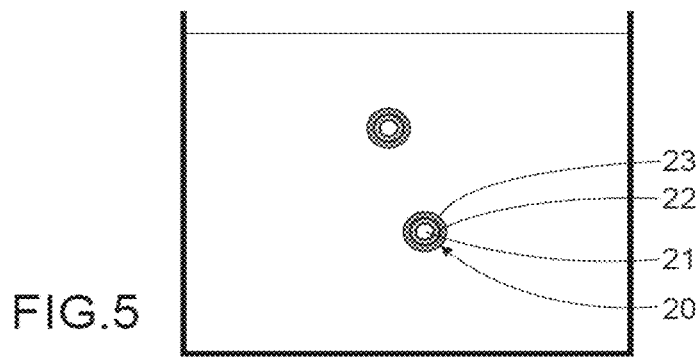

Contacting the monomers and the polymerisation initiator results in polymerisation of the monomers, whereby nanoparticles 20 coated with a layer of polymer material 23, dispersed in the organic phase 12, are obtained (FIGS. 3, 4 and 5).

During step a), an aqueous phase and an organic phase are contacted so as to obtain a biphasic mixture, then an emulsification of the biphasic mixture in the presence of a surfactant (or emulsifier) is carried out, whereby a water-in-oil emulsion 10, formed of droplets 11 of the aqueous phase dispersed in the organic phase 12 is obtained. The droplets 11 form micelles (hydrophilic core—hydrophobic tails).

The emulsification is, for example, formed by stirring (sonication). The mixture remains stable thanks to the addition of emulsifier. The velocity or evolution kinetics of the mixture is quasi-nil, which makes it a confined reaction medium that is particularly stable and favourable for polymer synthesis by monomer polymerisation.

The emulsion 10 may contain further, non-reactive, ingredients, but necessary for emulsion stabilisation.

Figure 6:
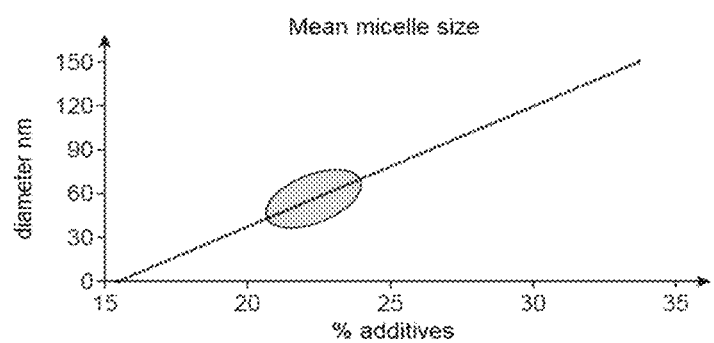
FIG. 6 is a graph representing the mean micelle size obtained by dynamic light scattering (DLS) according to the percentage (by weight) of additives in the aqueous phase.

As represented in FIG. 6, the size of the micelles 11 varies according to the quantity of surfactants (additives) present in the emulsion. On the other hand, the size of the micelles 11 does not change with the addition of the nanoparticles. Size denotes herein and hereinafter the mean size.

Preferably, the emulsion 10 is a miniemulsion, i.e. the droplets 11 dispersed, in the organic phase 12, have a size ranging from 20 nm to 1 µm, preferably from 30 nm to 100 nm, and more preferentially from 30 nm to 60 nm. The size of the droplets 11 will be chosen according to the size of the nanoparticles 20 and the thickness of the layer of polymer 23 sought.

During step b), nanoparticles 20 are added to the previously formed emulsion.

Nanoparticles denote elements of submicronic size (typically less than 1 µm) of spherical, elongated, ovoid shape, for example. Preferably, they consist of spherical particles. The greatest dimension thereof is referred to as diameter or size.

They may have a wide size distribution, for example have a diameter ranging from 5 nm to 1 µm. This size may be determined by photon correlation spectroscopy.

Figure 7:
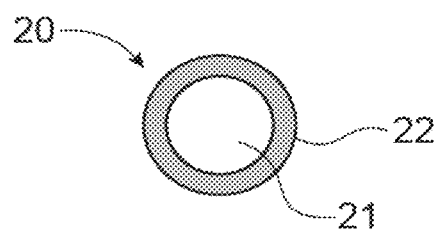
FIGS. 7 and 8 represent, schematically, and as a sectional view, nanoparticles before and after coating with a polymer layer, according to particular embodiments of the invention.

As represented in FIG. 7, the particles 20 have a core-shell structure. The shell 22 is rigidly connected to the core 21 of the particle.

The core 21, or kernel, is a metallic material. Metallic material denotes a metal or a metal alloy. Preferably, it consists of a metal. Preferably, it consists of cobalt, nickel, iron, copper, silver or gold. It may also consist of one of the alloys thereof, such as alloys of cobalt and iron (CoFe), of cobalt, iron and nickel (CoFeNi), of nickel and iron (NiFe) or one of the nitrides thereof, such as iron nitride $Fe_4N$ or $Fe_{16}N_2$.

The core 21 is coated with a coating 22 or shell. The coating 22 is made of an organic or inorganic carbonaceous material. Preferably, it consists of an inorganic coating 22.

The coating is an organised 2D carbon coating on a non-planar surface (for example on the surface of a nanoparticle).

Preferably, the coating 22 is made of graphene. It may comprise one layer or a plurality (two, three, four, etc.) layers of graphene. For example, it comprises from 1 to 50 lamellae of graphene, preferably from 2 to 10, for example from 2 to 5, and even more preferentially from 3 to 10.

Preferably, the carbonaceous shell 22 is continuous so as to fully cover the core 21 of the particle 20 to protect the core of the nanoparticles from oxidation, and render same more hydrophilic.

The nanoparticles 20 added in step b) are annotated as metal/C nanoparticles.

The nanoparticles 20 may be manufactured by flame, laser or plasma spray pyrolysis (SP), or by chemical vapour deposition (CVD). This type of powder has a substantial size distribution.

The carbonaceous shell 22 may be manufactured by decomposition of a precursor gas containing carbon, for example acetylene, by SP or CVD.

The emulsion will make it possible to sort these nanoparticles 20 according to the size thereof. For example, for a powder wherein the mean diameter of the nanoparticles 20 is of the order of 30 nm, the size dispersion is wide and can range from less than 5 nm to more than 300 nm. This is detrimental for the manufacture of a nanocomposite material with controlled properties.

Preferably, the size of the micelles 11 is 2 to 3 times greater than the mean size of the nanoparticles 20 (for example between 60 and 90 nm for 30 nm). Only the nanoparticles 20 of mean size of the order of 30 nm will be trapped in the emulsion and only these nanoparticles 20 will be subsequently coated with a layer of polymer 23. In this way, the largest nanoparticles 20 (for example 100 nm or 300 nm) will form a sediment not coated with polymer which will be readily subsequently removed. The smallest nanoparticles 20 (for example of 10 nm and less) imperfectly coated with carbonaceous coating 22 are oxidised rapidly (formation of carboxyls and/or metal oxides), and therefore more hydrophobic, remain in the organic phase (FIGS. 1 to 4).

Figure 2:
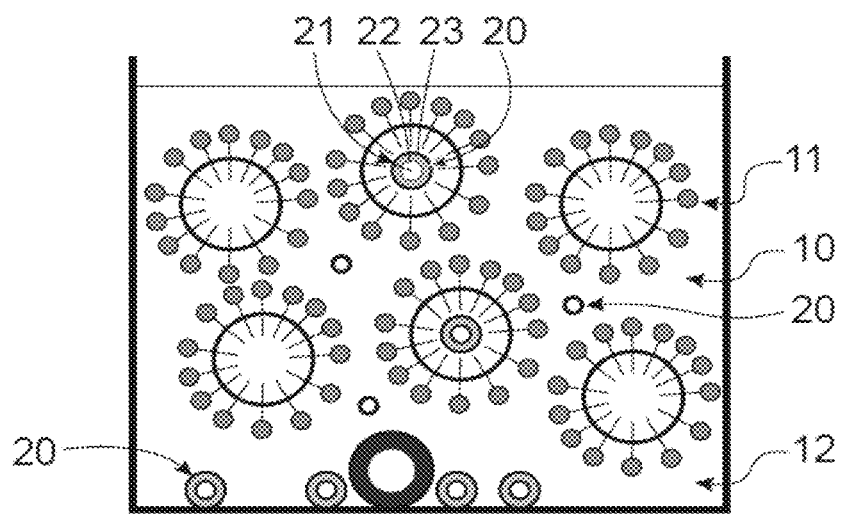

As represented in FIG. 2, about one third of the nanoparticles 20 of diameter of interest are stabilised in the micelles 11. The other nanoparticles 20 are suspended in the organic phase or in the sediment, and are not involved in polymerisation.

According to the size of the nanoparticles 20, a micelle 11 may contain a single nanoparticle 20 or a plurality of nanoparticles 20, for example in aggregate form. Advantageously, a micelle 11 contains a single nanoparticle 20.

According to an alternative embodiment of the method, not shown, the emulsion 10 further includes hydrophobic elements. The hydrophobic elements are dispersed in the dispersing phase (i.e. the organic phase). Preferably, the elements are electrically insulating. Electrically insulating denotes an intrinsic electrical resistivity greater than $10^{12}$ ohm·cm.

They may consist of mineral nanoparticles, for example silica nanoparticles, nanoparticles of complex oxides, for example of barium titanate ($BaTiO_3$) or/and strontium titanate ($SrTiO_3$), diamond nanoparticles and/or silicon carbide (SiC) nanoparticles.

They may consist of tubular or lamellar nanoparticles.

Tubular or lamellar nanoparticles denote particles wherein one of the dimensions is substantially less than the two others. Such tubular or lamellar particles most frequently have a thickness e (or a diameter d) substantially less than the length L or width I thereof. Preferably, the ratio e/L (or d/L) and e/I (or d/I) is less than or equal to 0.5 and preferably less than or equal to 0.1 or 0.01.

Advantageously, the tubular or lamellar nanoparticles are made of hexagonal boron nitride (h-BN). They may also consist of graphene oxide GO.

The lamellar nanoparticles may, for example, be exfoliated. Exfoliated denotes that lamellae or sheets of the stack forming the lamellar nanoparticles are removed so as to obtain lamellar particles formed from one or a few sheets (2, 3, 4 or 5 for example). The tubular nanoparticles may be manufactured by precursor gas decomposition by SP or by CVD.

In the emulsion 10, formed in step b), the polymerisation initiator and the monomers, precursors of the polymer, are added. Advantageously, quantities of initiator and monomer are chosen so as to obtain a low polymerisation yield in order to create a very thin layer 23 of polymer on the surface of the nanoparticles 20 (for example from 5 nm to 10 nm). Low denotes a polymerisation yield less than 50%, and preferably less than 25%, preferentially less than 20%, for example of the order of 10%. The quantity of monomers consumed is determined by the polymerisation yield.

Advantageously, the polymer is chosen among polystyrene (PS), poly(methyl methacrylate) (PMMA), polyurethane (PU), a polyacrylic (PAA), polypropylene (PP), a polyimide (PI) and polyetherimide (PEI). The polymer may also be a polymer functionalised by a conjugated pi group, such as pyrene. It consists, for example, of polystyrene functionalised by a pyrene group (Py-PS) or indeed a polyacrylic functionalised by a pyrene group (Py-PAA).

According to a first alternative embodiment, steps c) and d) are carried out simultaneously.

According to a further alternative embodiment, the method successively includes steps c), d) and c).

According to a further embodiment, step c) is carried out before step b).

When the polymer precursors are contacted with the polymerisation initiator, polymerisation is initiated (FIG. 3).

The polymerisation is a radical polymerisation. This is initiated by the entry into the micelle 11 of a (hydrophilic) oligo-radical previously formed in aqueous phase which will induce progressive consumption of the (hydrophobic) monomers stored in the dispersing phase (herein oil), until the micelle is saturated.

Conditions suitable for reacting the polymerisation primer are set up, typically by raising the temperature and/or by sonication.

For example, the polymerisation is performed by heating the emulsion to a temperature from 40° C. to 80° C., preferably from 50° C. to 80° C., and preferentially from 60° C. to 70° C. These temperature ranges may be adapted according to the temperature at which the polymerisation primer becomes reactive.

The polymerisation step generally lasts from some minutes to some tens of minutes, for example about 20 minutes. This step may be performed under ultrasound using a sonication probe.

Following the polymerisation step (FIG. 4), the droplets 11 of the emulsion 10 are converted into solid elements dispersed in the organic phase. "Dispersion" denotes a stable suspension of solid elements, preferably individualised and not agglomerated, in a liquid continuous phase. The elements have a mean size equivalent to the mean size of the droplets 11 of the emulsion 10 from which they originate.

Figure 8:
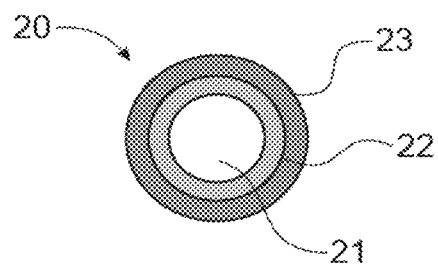
Figure 9:
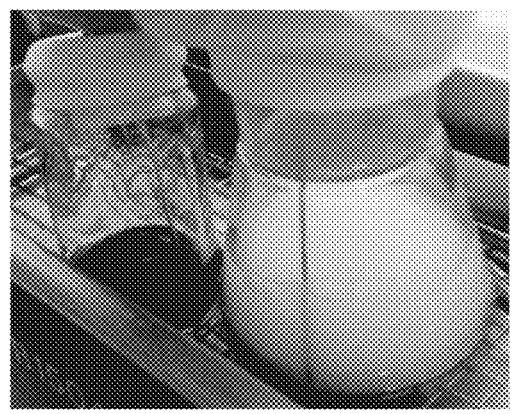
FIG. 9 is a photographic image showing a dispersion comprising a solvent and metal/C nanoparticles (on left) and a stabilised emulsion (on right) according to a particular embodiment of the method according to the invention.
Figure 10:
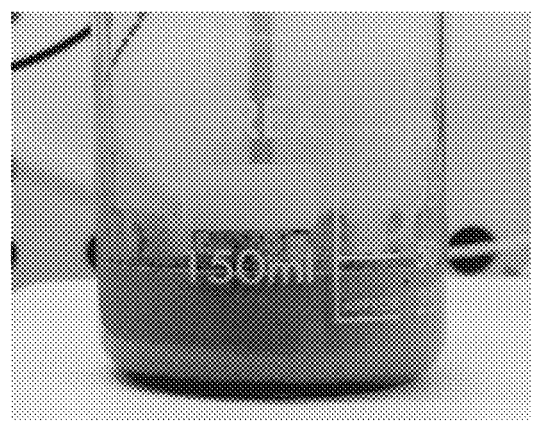
FIG. 10 is a photographic image showing a uniform suspension of metal/C nanoparticles coated with a thin layer of polymer, obtained according to a particular embodiment of the invention.

The solid elements may be beads 30 of polymer material, obtained in the case where the micelles do not contain, at the time of polymerisation, metal/C nanoparticles 20. Alternatively, as represented in FIG. 8, the solid elements may be metal/C nanoparticles 20 coated with a layer of polymer 23, annotated as metal/C/polymer, in the case where the micelles contain, at the time of polymerisation, metal/C nanoparticles 20.

In the case where a micelle 11 includes, at the start of the polymerisation step, a plurality of nanoparticles 20, the layer of polymer 23 coats all of these nanoparticles 20.

The method makes it possible to graft a layer 23 of polymer covalently to the surface of the nanoparticles 20.

The method is carried out at ambient pressure (1 bar) in a hermetic chamber, for example made of glass. The method is, advantageously, carried out with nitrogen bubbling to deoxygenate the reaction medium.

Following the polymerisation step, a "wash" (precipitation/dilution sequence) is advantageously carried out to remove the unused reaction products and retrieve the latex. The latex, similar to a cohesive powder, consists of metal/C/polymer nanoparticles 20, of very homogeneous size (for example 40 nm±2 nm), and of polymer beads 30 (FIG. 4).

A centrifugation separation step may then be carried out to separate the metal/C/polymer nanoparticles from the polymer beads (FIG. 5). About one third of the nanoparticles 20 introduced may thus be retrieved.

The nanoparticles 20 obtained with the method form a powder. The nanoparticles are monodispersed, i.e. they have a size distribution between a maximum diameter and a minimum diameter such that the ratio thereof is less than or equal to 5, 3 or 2 and advantageously less than or equal to 1.5 for example 1.3 or 1.2 or 1.1. The characteristics of such a powder (ratio 1.1) are, for example, a mean nanoparticle diameter of 40 nm, a maximum diameter of 42 nm and a minimum diameter of 38 nm. The diameter of the nanoparticles 20 may be measured with a laser granulometer or by dynamic light scattering (DLS) in solution.

All the dimensional characteristics mentioned above and hereinafter may also be measured using the following techniques: SEM (scanning electron microscope) and TEM (transmission electron microscope), ellipsometry and spectrophotometry.

The metal/C/polymer nanoparticles 20 may subsequently be used to produce another material. For example, they may be dispersed in a solvent and form a stable colloidal solution. They may be dispersed in a mineral matrix or in a polymer matrix, the polymer being identical to or different from that of the shell. It may consist of a thermoplastic polymer or of a photosensitive resin. By way of illustration, they may be coated in a polymer matrix (for example made of polystyrene, epoxy or polyimide) so as to form a uniform metal-polymer nanocomposite film.

The polymer matrix, for example made of PI or epoxide, may contain photosensitive cross-linking agents, preferably to ultraviolet (UV).

This film may be formed, on a substrate, for example made of silicon, by spin coating. Further deposition techniques may be envisaged, such as dip coating, screen printing, or ink jet. A deposition technique wherein the temperatures involved do not exceed the melting point of the polymer shell of the nanoparticle will be chosen.

The film may be exposed to a light source, preferably to an ultraviolet (UV) source. The film may be hot-pressed, preferably in the vicinity of the glass transition temperature.

Such a film contains a homogeneous dispersion of metallic nanoparticles with a narrow size dispersion. Furthermore, as the nanoparticles are solidly coated with an even thin layer of dielectric polymer, the separating distance between the nanoparticles is controlled. For example, the edge-to-edge separating distance between two metal/C particles of diameter $\phi$ is $1\times\phi$, $\frac{1}{2}\times\phi$ or $\frac{2}{3}\times\phi$ and advantageously less than or equal to $\frac{1}{3}\times\phi$. For example, such a film is characterised by a homogeneous dispersion of Co/C nanoparticles of mean diameter 30 nm with a mean intergranular distance of 10 nm, up to 5 nm.

The volume percentage of nanoparticles in the composite material ranges, for example, from 0.01 to 30%.

Advantageously, to form a capacitor, the volume percentage ranges for example from 0.01% to 10%, for example from 0.01% to 5%, and preferably from 0.1% to 2%.

Advantageously, for inductors or filters, the volume percentage is greater than 10%, for example from 10% to 30%, or greater than 30%. The mass percentage of nanoparticles in the composite material ranges, for example, from 0.5% to 90%, and preferably from 0.5% to 10% for capacitors and from 50% to 90% for inductors or filters.

Such a film has a high resistivity (for example $10^{12}$-$10^{15}$ μOhm·cm).

Such a composite material may, for example, form an electronic device element such as an inductor, a filter or a capacitor, and more particularly an inductor or a filter made of thin layers on silicon or on ferrite or a capacitor made of thin layers on silicon. Such an inductor and such a filter may be used for the integration of RF filtering or power conversion modules, for example for 5G telephony. Such a capacitor may be used for the integration of power conversion modules, for example for electric vehicles.

Illustrative and Non-Limiting Examples of an Embodiment

Nanoparticles used: Co/C, diameter 30-50 nm
Products and conditions used for in-situ polymerisation:
Monomer: Styrene 99%,
Surfactant: sodium deoxycholate (DOC) 97%,
Initiator: 2,2'-azobis (2-methyl propionitrile) (AIBN) 98%,
Proportion: DOC+AIBN=1% Styrene (by weight),
Reaction temperature=65° C.,
$N_2$ bubbling,
Sonication: 500 W at 20 kHz,
Duration: 20 to 30 min.
Products and conditions used to retrieve latex (precipitation/washing):
Emulsion product (raw latex, monomer residues, initiator, surfactant),
Precipitation solvent: methanol 98%,
Dilution solvent (Styrene): toluene 98%,
Precipitation/dilution sequence repeated 4 times,
Vacuum air drying.

Products and conditions used to retrieve polymer-coated nanoparticles:
- Washed latex (coated nanoparticles and polymer nanobeads),
- Solvent: chloroform 98%,
- Stirring+Centrifugation at $12\ 10^3$ rpm for 20 min,
- Retrieval of the supernatant,
- Sequence repeated 4 times, Products and conditions used for deposition of a film comprising the polymer-coated nanoparticles:
- Coated particles,
- Solvent: chloroform 98%,
- Addition of substrate polymer: Polystyrene 0.75 g/mL (35 kg/mol),
- Sonication: 500 W at 20 kHz,
- Duration: 20 min,
- Spin-coating: 1000 rpm,
- Drying on hot plate at 65° C. for 10 min.

Figure 11:
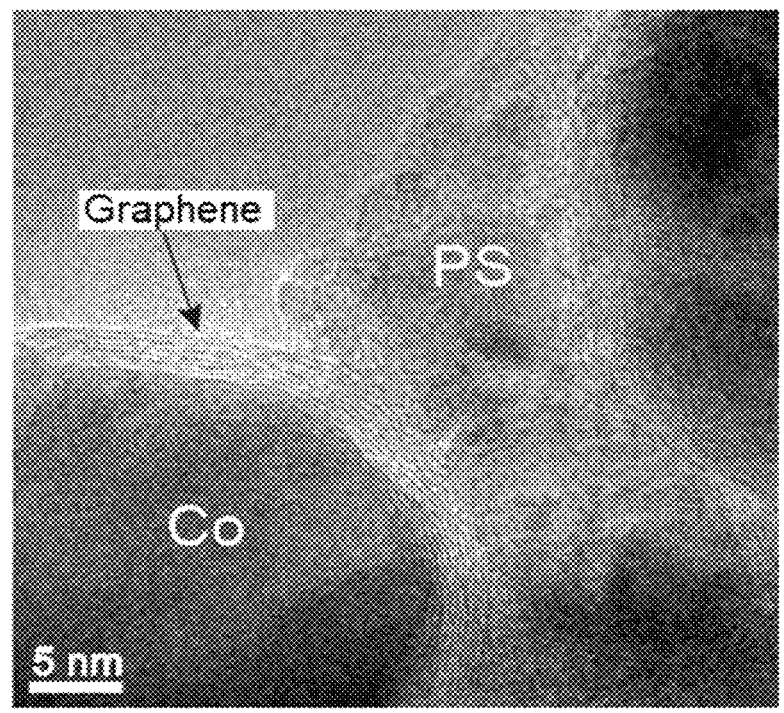
FIG. 11 is an image obtained by transmission electron microscopy of core/shell structure nanoparticles obtained according to a particular embodiment of the method according to the invention.

The grafted polymer thickness on the surface of the Co/C nanoparticles is of the order of 5 nm (FIG. 11).

Figure 12A:
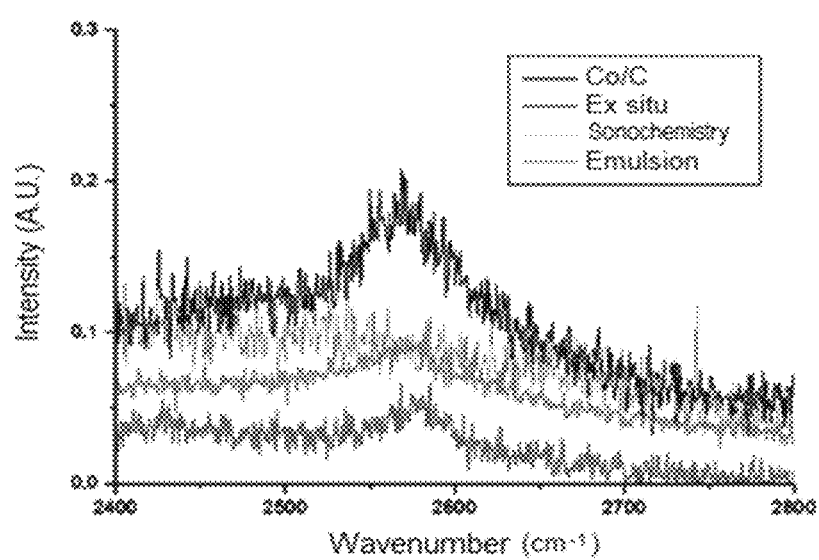
FIGS. 12a and 12b are Raman spectra centred, respectively, on the main line of graphene and on the main line of cobalt oxide, obtained on Co/C nanoparticles, Co/C nanoparticles coated with a layer of polymer according to a non-covalent grafting method in homogeneous medium with pre-existing polymer (designated by 'ex-situ'), Co/C nanoparticles coated with a layer of polymer according to a covalent grafting method with in-situ polymerisation in homogeneous medium by sonochemistry (designated by 'sonochemistry'), Co/C nanoparticles coated with a layer of polymer according to a particular embodiment of the method according to the invention, i.e. a covalent grafting method with in-situ polymerisation in heterogeneous medium or miniemulsion (designated by 'emulsion').
Figure 12B:
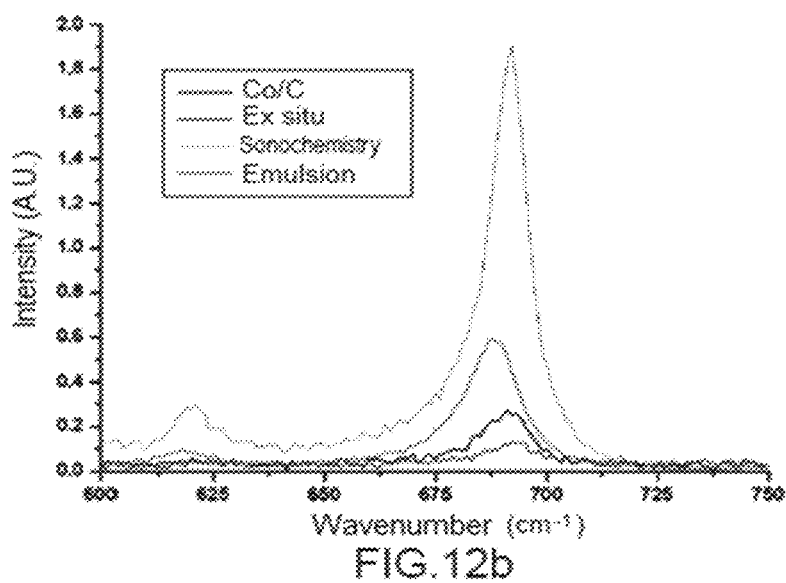

The Raman spectra obtained on these nanoparticles 20 show that the carbon layer is not damaged and/or that the oxidation is contained, unlike other techniques routinely used for coating nanoparticles such as in-situ polymerisation in homogeneous medium (or sonochemistry), or such as a technique consisting of coating nanoparticles 20 with a previously separately (or ex-situ) polymerised polymer (FIGS. 12a and 12b).

The same results were observed for Ni/C nanoparticles coated with a polystyrene layer.

The invention claimed is:

1. A method for manufacturing nanoparticles comprising a metallic core coated with a layer of polymer material comprising the following steps:
    a) preparing a water-in-oil emulsion comprising droplets of an aqueous phase, dispersed in an organic phase,
    b) adding nanoparticles comprising a metallic core comprising cobalt iron, nickel, copper, silver, gold, or one of the alloys thereof coated with a continuous shell of graphene, whereby nanoparticles trapped in the droplets are obtained,
    c) adding precursor monomers of the polymer material, and
    d) adding a polymerisation initiator,
    adding the precursor monomers of the polymer material and the polymerisation initiator resulting in polymerisation of the monomers, whereby nanoparticles coated with a layer of polymer material, dispersed in the organic phase, are obtained.

2. The method according to claim 1, wherein the polymer material is chosen among polystyrene, poly(methyl methacrylate), polyurethane, a polyacrylic, polypropylene, a polyimide, polyetherimide and a polymer having a pyrene group.

3. The method according to claim 1, wherein the thickness of the layer of polymer material ranges from 1 nm to 100 nm.

4. The method according to claim 3, wherein the thickness of the layer of polymer material ranges from 2 nm to 50 nm.

5. The method according to claim 1, wherein the diameter of the droplets ranges from 20 nm to 1 μm.

6. The method according to claim 5, wherein the diameter of the droplets ranges from 30 nm to 100 nm.

7. The method according to claim 1, wherein electrically insulating nanoparticles are added to the emulsion.

8. The method according to claim 7, wherein the electrically insulating nanoparticles are made of metal oxide.

9. The method according to claim 7, wherein the electrically insulating elements are hydrophobic and in the organic phase.

10. The method according to claim 7, wherein the electrically insulating elements are at least one selected from the group consisting of silica nanoparticles, barium titanate ($BaTiO_3$), strontium titanate ($SrTiO_3$), and diamond nanoparticles.

11. The method according to claim 1, wherein in a), the water-in-oil emulsion comprises droplets of the aqueous phase dispersed in the organic phase, wherein the droplets form micelles, wherein the size of the micelles is 2 to 3 times greater than the size of the nanoparticles.

* * * * *